United States Patent
Tom et al.

(10) Patent No.: US 8,816,692 B2
(45) Date of Patent: Aug. 26, 2014

(54) TEST SYSTEM FOR A BATTERY MODULE

(75) Inventors: Kwok Tom, Madison Heights, MI (US); William Koetting, Davisburg, MI (US); Steve Howay, Metamora, MI (US)

(73) Assignee: LG Chem, Ltd., Seoul (KR)

( * ) Notice: Subject to any disclaimer, the term of this patent is extended or adjusted under 35 U.S.C. 154(b) by 431 days.

(21) Appl. No.: 13/308,817

(22) Filed: Dec. 1, 2011

(65) Prior Publication Data

US 2013/0141105 A1   Jun. 6, 2013

(51) Int. Cl.
  G01N 27/416   (2006.01)
  G01N 27/00   (2006.01)
  G01N 27/27   (2006.01)

(52) U.S. Cl.
  CPC ............... *G01N 27/00* (2013.01); *G01N 27/27* (2013.01)
  USPC ........................................... 324/426

(58) Field of Classification Search
  CPC ....... G01N 27/00; G01N 27/27; G01N 27/28; G01N 27/283
  USPC .......... 320/107, 132, 150; 429/426, 427, 431, 429/433
  See application file for complete search history.

(56) References Cited

U.S. PATENT DOCUMENTS

| | | | |
|---|---|---|---|
| 4,214,204 A | 7/1980 | Eberle | |
| 4,311,917 A | 1/1982 | Hencey, Jr. et al. | |
| 4,363,407 A | 12/1982 | Buckler et al. | |
| 5,357,423 A | 10/1994 | Weaver et al. | |
| 5,901,572 A | 5/1999 | Peiffer et al. | |
| 6,138,466 A | 10/2000 | Lake et al. | |
| 6,762,610 B1 | 7/2004 | Brilmyer et al. | |
| 7,109,700 B2 | 9/2006 | Fazzina | |
| 7,915,856 B2 | 3/2011 | Krampitz et al. | |
| 7,974,797 B2 | 7/2011 | Shoji | |
| 8,487,631 B2 | 7/2013 | Yuasa et al. | |
| 2001/0019270 A1 | 9/2001 | Onishi et al. | |
| 2002/0062650 A1 | 5/2002 | Dukhan et al. | |
| 2002/0193955 A1 | 12/2002 | Bertness et al. | |
| 2003/0139888 A1 | 7/2003 | Burns | |
| 2004/0108856 A1 | 6/2004 | Johnson | |
| 2004/0204172 A1 | 10/2004 | Herle | |

(Continued)

FOREIGN PATENT DOCUMENTS

| | | |
|---|---|---|
| GB | 2291737 A | 1/1996 |
| JP | S5999271 A | 6/1984 |

(Continued)

OTHER PUBLICATIONS

International Search Report for International application No. PCT/KR2012/009014 dated Feb. 28, 2013.

*Primary Examiner* — Edward Tso
(74) *Attorney, Agent, or Firm* — Buckert Patent & Trademark Law Firm, P.C.; John F. Buckert

(57) ABSTRACT

A test system for a battery module is provided. The system includes a housing having a bottom plate; and first, second, third and fourth side walls coupled to the bottom plate that defines an interior region. The system further includes a mounting fixture that fixedly holds the battery module thereon. The system further includes first, second, third and fourth coupling members. The system further includes a lid coupled to the housing utilizing the first, second, third and fourth coupling members. The system further includes a battery charging system that charges the battery module.

16 Claims, 4 Drawing Sheets

(56) References Cited

U.S. PATENT DOCUMENTS

| | | |
|---|---|---|
| 2005/0134283 A1 | 6/2005 | Potempa |
| 2005/0257533 A1 | 11/2005 | Gunawardana et al. |
| 2005/0264296 A1 | 12/2005 | Philbrook |
| 2006/0012341 A1 | 1/2006 | Burns |
| 2007/0252555 A1 | 11/2007 | Potempa |
| 2007/0261415 A1 | 11/2007 | Barnes |
| 2008/0231257 A1 | 9/2008 | Williams |
| 2008/0290877 A1 | 11/2008 | Oh et al. |
| 2009/0243621 A1 | 10/2009 | Kudo et al. |
| 2009/0251149 A1 | 10/2009 | Buckner et al. |
| 2010/0102975 A1 | 4/2010 | Vossmeyer et al. |
| 2011/0050235 A1 | 3/2011 | Bogdan, Jr. et al. |
| 2011/0116225 A1 | 5/2011 | Staben et al. |
| 2011/0254558 A1 | 10/2011 | Stancu et al. |
| 2011/0256430 A1 | 10/2011 | Stancu et al. |
| 2011/0300416 A1* | 12/2011 | Bertness .................. 429/49 |
| 2013/0015702 A1 | 1/2013 | Ito |
| 2013/0119937 A1 | 5/2013 | Arseneault et al. |
| 2014/0084934 A1 | 3/2014 | Bober |

FOREIGN PATENT DOCUMENTS

| | | |
|---|---|---|
| JP | H0797004 A | 4/1995 |
| JP | H08185896 A | 7/1996 |
| JP | H1140212 A | 2/1999 |
| JP | 2002343318 A | 11/2002 |
| JP | 2005228659 A | 8/2005 |
| JP | 2007280794 A | 10/2007 |
| JP | 2010236981 A | 10/2010 |
| KR | 20040072069 A | 8/2004 |
| KR | 20050001008 A | 1/2005 |
| KR | 20060068172 A | 6/2006 |
| KR | 20090015273 A | 2/2009 |
| KR | 20100003136 A | 1/2010 |

* cited by examiner

TEST SYSTEM FOR A BATTERY MODULE

BACKGROUND

Battery modules have been tested in an open air environment. The inventors herein have recognized a need for an improved test system that tests a battery module in an enclosed housing during extreme operational or environmental conditions.

SUMMARY

A test system for a battery module in accordance with an exemplary embodiment is provided. The test system includes a housing having a bottom plate; and first, second, third and fourth side walls coupled to the bottom plate that defines an interior region. The first and third walls are disposed substantially parallel to one another. The test system further includes a mounting fixture configured to fixedly hold the battery module thereon. The mounting fixture is coupled to the bottom plate within the interior region. The test system further includes first, second, third and fourth coupling members. The first and second coupling members are coupled to an upper end of the first wall. The third and fourth coupling members are coupled to an upper end of the third wall. The test system further includes a lid coupled to the housing utilizing the first, second, third and fourth coupling members. The test system further includes a battery charging system configured to charge the battery module while the battery module is fixedly held in the mounting fixture.

DETAILED DESCRIPTION

Figure 1:
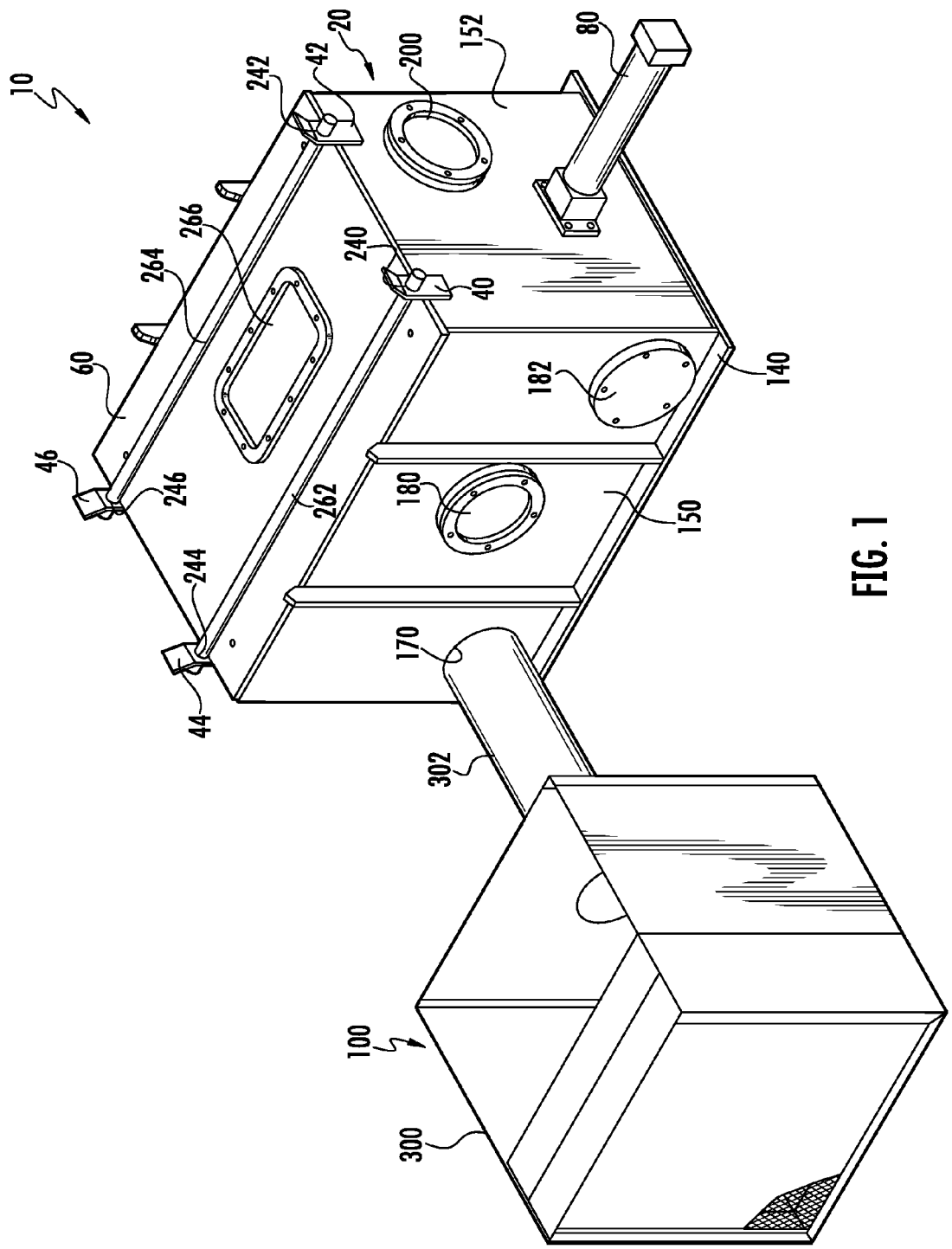
FIG. 1 is a schematic of a test system in accordance with an exemplary embodiment.
Figure 2:
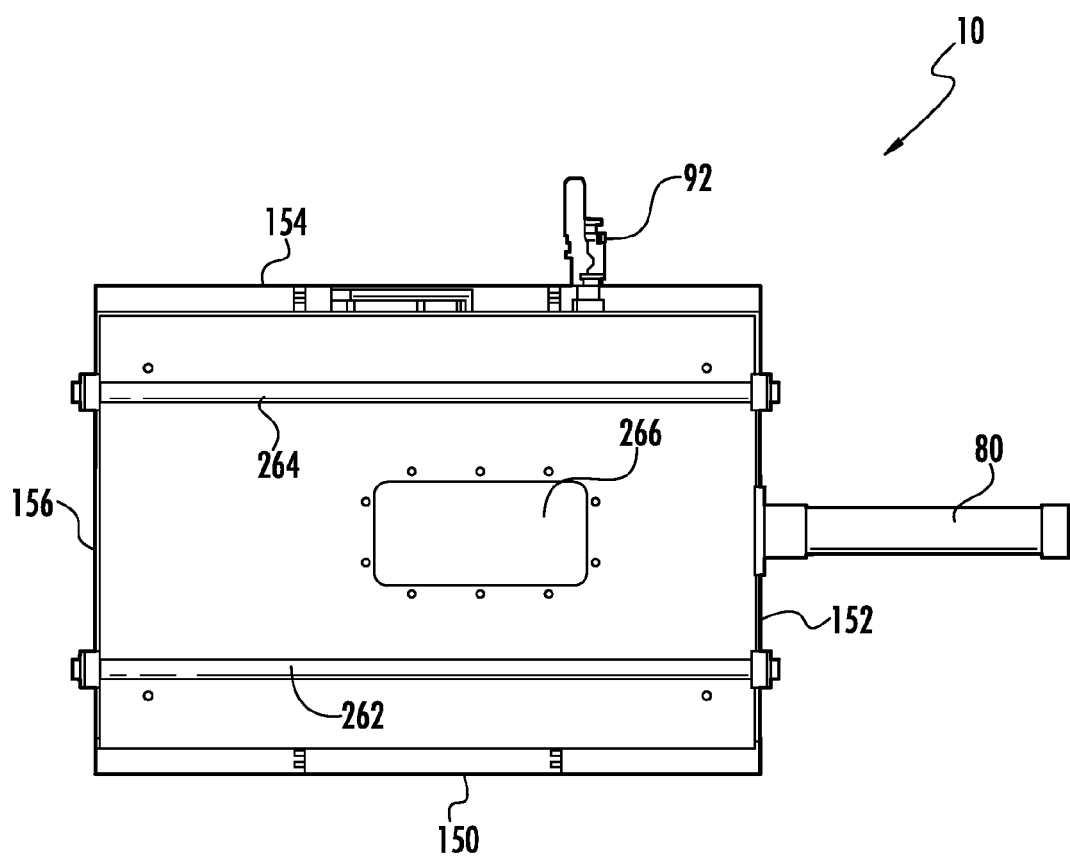
FIG. 2 is a top view of a portion of the test system of FIG. 1.

Referring to FIGS. 1-4, a test system 10 for testing a battery module 12, in accordance with an exemplary embodiment is provided. The test system 10 includes a housing 20, a mounting fixture 30, coupling members 40, 42, 44, 46, a lid 60, battery charging system 70, an actuatable cylinder 80, an argon gas delivery system 90, a valve 92, a vacuum system 100, a voltage sensor 110, a temperature sensor 111, and a computer 120.

The housing 20 is configured to hold the mounting fixture 30 and the battery module 12 therein. The housing 20 includes a bottom plate 140, and side walls 150, 152, 154, 156 couple to the bottom plate 140 that define an interior region 160. The side walls 150, 154 are disposed generally parallel to one another. Further, the side walls 152, 156 are disposed substantially parallel to one another. In one exemplary embodiment, the bottom plate 140, and the side walls 150, 152, 154, 156 are constructed of steel.

The side wall 150 includes apertures 170, 172, 174 extending therethrough. A viewing window 180 is disposed over the aperture 172 and is coupled to the side wall 150. Also, a circular plate 182 is disposed over the aperture 174 and is coupled to the side wall 150. Further, a pipe 302 is received within the aperture 170, as will be explained in greater detail below.

The side wall 152 includes apertures 190, 192 extending therethrough. A viewing window 200 is disposed over the aperture 192 and is coupled to the side wall 152. The aperture 190 is configured to receive a rod 280 from the actuatable cylinder 80 therethrough.

The side wall 154 includes an aperture 210 extending therethrough. A data cable 122 that couples the computer 120 to the voltage sensor 110 within the housing 20, extends through the aperture 210 of the housing 20. Also, a cable 71 that couples the battery charging system 70 to the battery module 12 within the housing 20, extends through the aperture 20.

The mounting fixture 30 is configured to fixedly hold the battery module 12 thereon. The mounting fixture 30 is coupled to the bottom plate 140 within the interior region 160 of the housing 20 during testing of the battery module 12.

Figure 3:
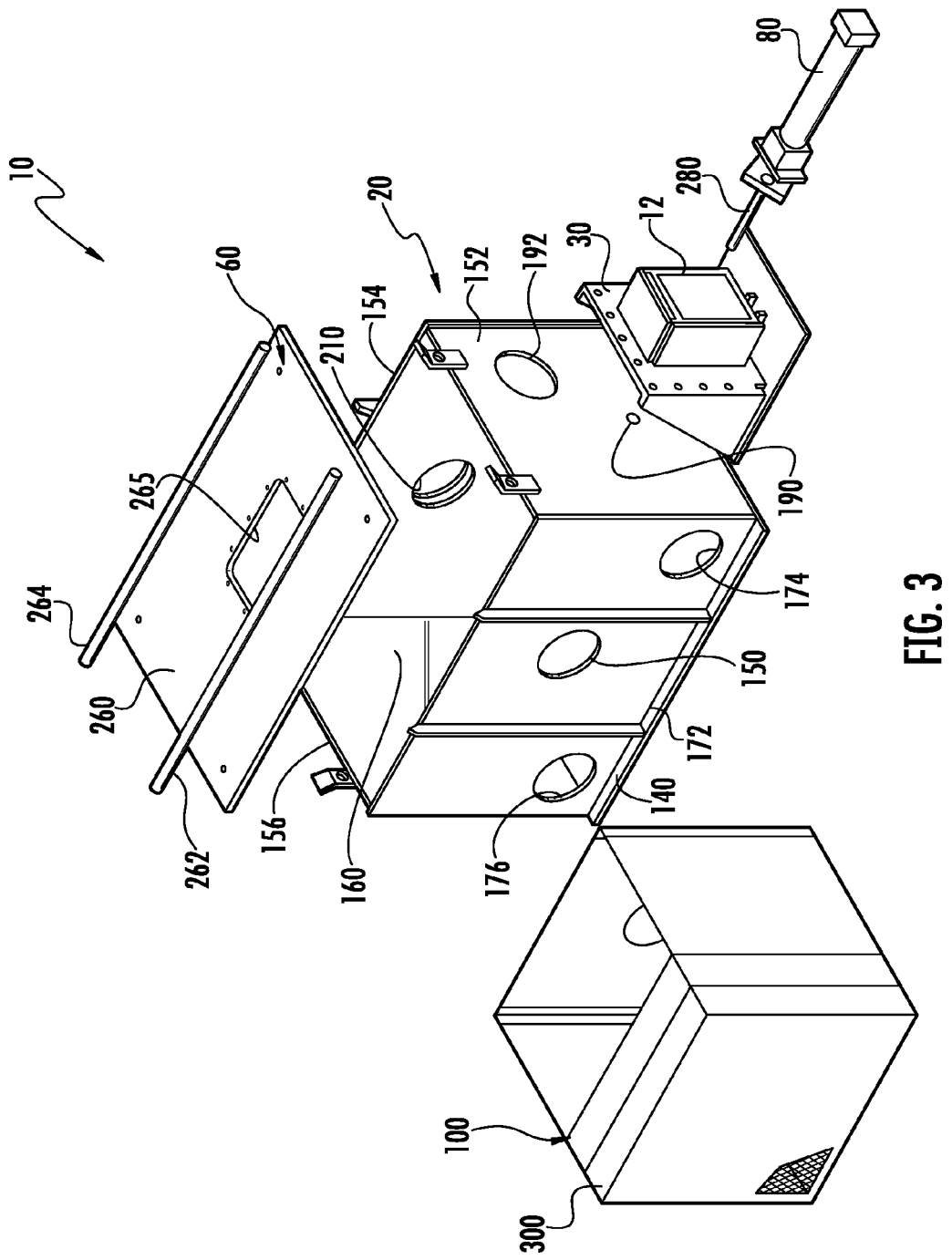
FIG. 3 is an exploded view of a portion of the test system of FIG. 1.

Referring to FIGS. 1 and 3, the coupling members 40, 42, 44, 46 are configured to removably couple the lid 60 on the housing 20. The coupling members 40, 42, 44, 46 are constructed of steel and include apertures 240, 242, 244, 246, respectively, extending therethrough. The coupling members 40, 42 are coupled to an upper end of the wall 152, and at least a portion of each of the coupling members 40, 42 extend above the wall 152. The coupling members 44, 46 are coupled to an upper end of the wall 156, and at least a portion of each of the coupling members 44, 46 extend above the wall 156.

The lid 60 is removably coupled to the housing 20 utilizing the coupling members 40, 42, 44, 46. The lid 60 includes a plate portion 260 and bars 262, 264 coupled to the plate portion 260. The plate portion 260 is configured to cover an upper open end of the housing 20, and in one exemplary embodiment, the plate portion 260 and the bars 262, 264 are constructed of steel. The bar 262 is configured to be received in the aperture 240 of the coupling member 40 and in the aperture 244 of the coupling member 44. The bar 264 is configured to be received in the aperture 242 of the coupling member 42 and in the aperture 246 of the coupling member 46. The plate portion 260 includes an aperture 265 extending therethrough. A viewing window 266 is disposed over the aperture 264 and is coupled to the plate portion 260.

Figure 4:
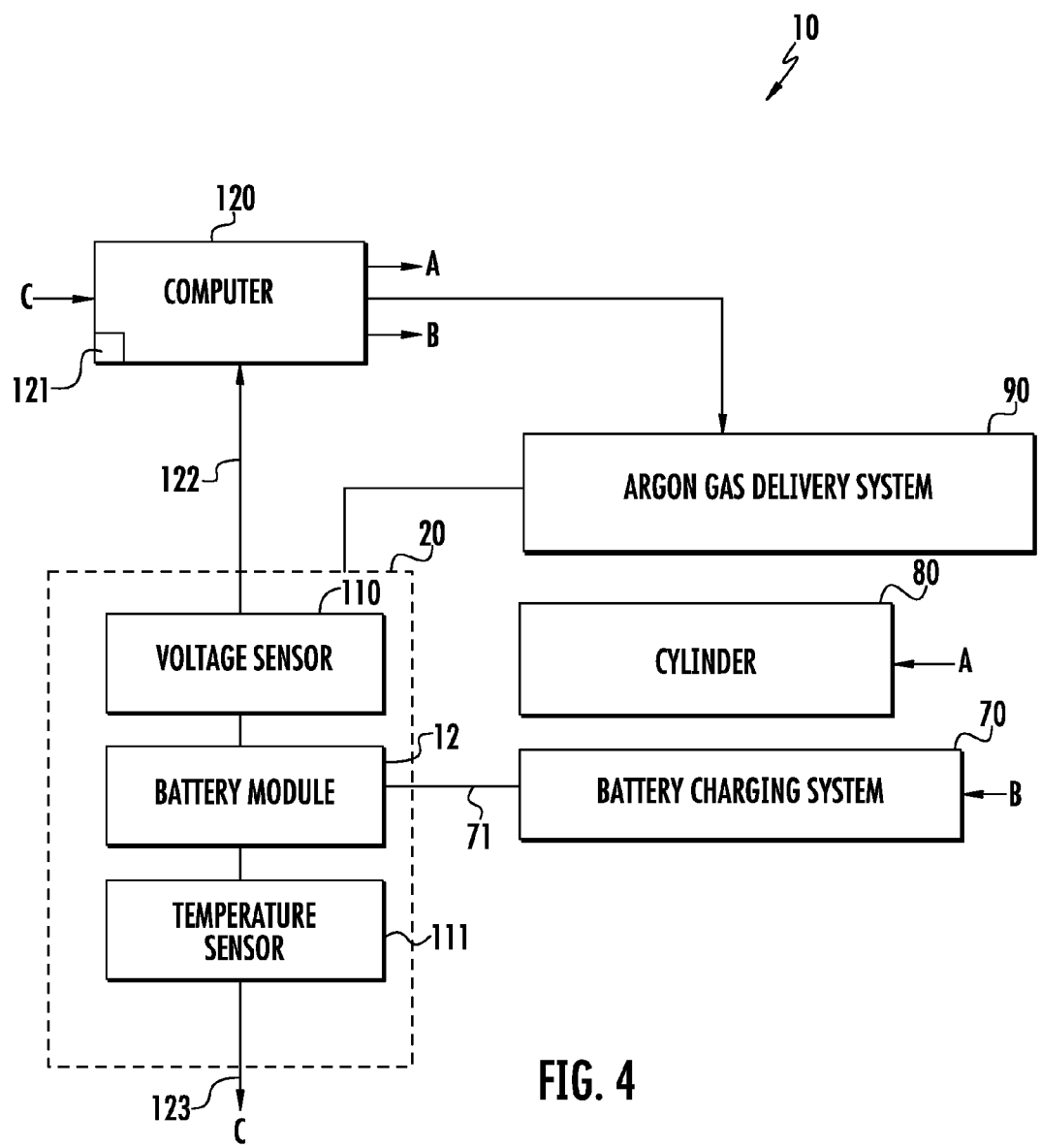
FIG. 4 is a block diagram of a portion of the test system of FIG. 1.

Referring to FIGS. 1, 3 and 4, the battery charging system 70 is configured to charge the battery module 12 while the battery module 12 is fixedly held in the mounting fixture 30 within the interior region 160. The battery charging system 70 has cables 71 that extend through the aperture 210 of the housing 20 and are coupled to the battery module 12. During one exemplary test, battery charging system 70 is configured to overcharge the battery module 12.

The actuatable cylinder 80 is coupled to the housing 20. The actuatable cylinder 80 is configured to extend the rod 280 from a first operational position to a second operational position in response to a control signal from the computer 120. In one exemplary puncture test, the computer 120 generates a control signal to induce the actuatable cylinder 80 to extend the rod 280 from the first operational position through the aperture 190 of the housing 22 to the second operational position such that the rod 280 penetrates at least a portion of the battery module 12. In one exemplary embodiment, the actuatable cylinder 80 is an electric cylinder. In another exemplary embodiment, the actuatable cylinder 80 is a hydraulic cylinder Referring to FIGS. 1-4, the argon gas delivery system 90 is configured to deliver argon gas through a valve 92 into the interior region 160 of the housing 20 in response to a control signal from the computer 120. The argon gas is utilized to reduce any thermal events within the housing 20.

The vacuum system 100 is configured to extract gases from the interior region 160 of the housing 20. The vacuum system 100 includes a vacuum device 300 having internal filters and a pipe 302. The pipe 302 is fluidly coupled between the vacuum device 300 and the aperture 170 extending through the housing 20.

At least one voltage sensor 110 is operably coupled to the battery module 12. The voltage sensor 110 is configured to generate a voltage signal indicative of an output voltage of at least one battery cell within the battery module 12 that is received by the computer 120. The computer 120 can make a determination as to whether the battery module 12 is overcharged based on the output voltage of at least one battery cell. The data cable 122 is coupled between the computer 120 and the voltage sensor 110, and extends through the aperture 210 of the housing 20.

At least one temperature sensor 111 is operably coupled to the battery module 12. The temperature sensor 111 is configured to generate a temperature signal indicative of a temperature of at least one battery cell within the battery module 12 that is received by the computer 120. The computer 120 is configured to determine a temperature value indicating a temperature of the at least one battery cell based on the temperature signal, and stores the temperature value in the memory device 121. The data cable 123 is coupled between the computer 120 and the temperatures sensor 111, and extends through the aperture 210 of the housing 20.

The computer 120 is operably coupled to the argon gas delivery system 90, the battery charging system 70, the voltage sensor 110, and the temperatures sensor 111. The computer 120 is configured to generate a control signal to induce the argon gas delivery system 90 to supply argon gas into the housing 20. The computer 120 is further configured to generate a control signal to induce the battery charging system 70 to charge the battery module 12. The computer 120 is further configured to receive the voltage signal from the voltage sensor 110 and to store a voltage value in an internal memory device 121 corresponding to the voltage value. The computer 120 is further configured to receive a temperature signal from the temperature sensor 111 and to store a temperature value in the internal memory device 121 corresponding to the temperature value. The internal memory device 121 further stores executable software instructions and associated data. In one exemplary embodiment, the computer 120 comprises a microprocessor operably coupled to a memory device. Of course, in alternative embodiments, the computer 120 could comprise a programmable logic controller or a field programmable logic array.

The test system 10 provides a substantial advantage over other test systems. In particular, the test system 10 holds the battery module 12 within an enclosed housing on a test fixture and charges the battery module 12 within the housing. Further, the test system 10 is configured to puncture the battery module 12 and to supply argon gas into the housing 20.

While the claimed invention has been described in detail in connection with only a limited number of embodiments, it should be readily understood that the invention is not limited to such disclosed embodiments. Rather, the claimed invention can be modified to incorporate any number of variations, alterations, substitutions or equivalent arrangements not heretofore described, but which are commensurate with the spirit and scope of the invention. Additionally, while various embodiments of the claimed invention have been described, it is to be understood that aspects of the invention may include only some of the described embodiments. Accordingly, the claimed invention is not to be seen as limited by the foregoing description.

What is claimed is:

1. A test system for a battery module, comprising:
a housing having a bottom plate; and first, second, third and fourth side walls coupled to the bottom plate that define an interior region; the first and third walls being disposed substantially parallel to one another;
a mounting fixture configured to fixedly hold the battery module thereon, the mounting fixture coupled to the bottom plate within the interior region;
first, second, third and fourth coupling members, the first and second coupling members coupled to an upper end of the first wall, the third and fourth coupling members coupled to an upper end of the third wall;
a lid coupled to the housing utilizing the first, second, third and fourth coupling members;
a battery charging system configured to charge the battery module while the battery module is fixedly held in the mounting fixture; and
the lid including a plate portion and first and second bars coupled to the plate portion, the plate portion configured to cover an upper open end of the housing, the first bar configured to be received in an aperture of the first coupling member and in an aperture of the third coupling member, the second bar configured to be received in an aperture of the second coupling member and in an aperture of the fourth coupling member.

2. The test system of claim 1, further comprising a vacuum system configured to extract gases from the interior region of the housing.

3. The test system of claim 1, further comprising an argon gas delivery system configured to deliver argon gas into the interior region of the housing.

4. The test system of claim 1, further comprising an actuatable cylinder coupled to the housing, the actuatable cylinder configured to extend a rod from a first operational position to a second operational position such that the rod penetrates the battery module at the second operational position.

5. The test system of claim 1, further comprising a voltage sensor configured to generate a voltage signal indicative of an output voltage of at least one battery cell within the battery module.

6. The test system of claim 5, further comprising a computer configured to receive the voltage signal and to store a voltage value in an internal memory corresponding to the voltage value.

7. The test system of claim 1, further comprising a temperature sensor configured to generate a temperature signal indicative of a temperature of at least one battery cell within the battery module.

8. The test system of claim 1, wherein at least one of the first, second, third and fourth side walls has an aperture extending therethrough, and a viewing window disposed in the aperture.

9. The test system of claim 1, wherein the plate portion of the lid has an aperture extending therethrough, and a viewing window disposed in the aperture.

10. The test system of claim 1, wherein the first, second, third and fourth side walls are constructed of steel.

11. The test system of claim 10, wherein the plate portion of the lid is constructed of steel.

12. A test system for a battery module, comprising:
a housing having a bottom plate; and first, second, third and fourth side walls coupled to the bottom plate that define an interior region; the first and third walls being disposed substantially parallel to one another;
a mounting fixture configured to fixedly hold the battery module thereon, the mounting fixture coupled to the bottom plate within the interior region;
first, second, third and fourth coupling members, the first and second coupling members coupled to an upper end of the first wall, the third and fourth coupling members coupled to an upper end of the third wall;
a lid coupled to the housing utilizing the first, second, third and fourth coupling members;
a battery charging system configured to charge the battery module while the battery module is fixedly held in the mounting fixture; and
a vacuum system configured to extract gases from the interior region of the housing.

13. A test system for a battery module, comprising:
a housing having a bottom plate; and first, second, third and fourth side walls coupled to the bottom plate that define an interior region; the first and third walls being disposed substantially parallel to one another;
a mounting fixture configured to fixedly hold the battery module thereon, the mounting fixture coupled to the bottom plate within the interior region;
first, second, third and fourth coupling members, the first and second coupling members coupled to an upper end of the first wall, the third and fourth coupling members coupled to an upper end of the third wall;
a lid coupled to the housing utilizing the first, second, third and fourth coupling members;
a battery charging system configured to charge the battery module while the battery module is fixedly held in the mounting fixture; and
an argon gas delivery system configured to deliver argon gas into the interior region of the housing.

14. A test system for a battery module, comprising:
a housing having a bottom plate; and first, second, third and fourth side walls coupled to the bottom plate that define an interior region; the first and third walls being disposed substantially parallel to one another;
a mounting fixture configured to fixedly hold the battery module thereon, the mounting fixture coupled to the bottom plate within the interior region;
first, second, third and fourth coupling members, the first and second coupling members coupled to an upper end of the first wall, the third and fourth coupling members coupled to an upper end of the third wall;
a lid coupled to the housing utilizing the first, second, third and fourth coupling members;
a battery charging system configured to charge the battery module while the battery module is fixedly held in the mounting fixture; and
an actuatable cylinder coupled to the housing, the actuatable cylinder configured to extend a rod from a first operational position to a second operational position such that the rod penetrates the battery module at the second operational position.

15. A test system for a battery module, comprising:
a housing having a bottom plate; and first, second, third and fourth side walls coupled to the bottom plate that define an interior region; the first and third walls being disposed substantially parallel to one another;
a mounting fixture configured to fixedly hold the battery module thereon, the mounting fixture coupled to the bottom plate within the interior region;
first, second, third and fourth coupling members, the first and second coupling members coupled to an upper end of the first wall, the third and fourth coupling members coupled to an upper end of the third wall;
a lid coupled to the housing utilizing the first, second, third and fourth coupling members;
a battery charging system configured to charge the battery module while the battery module is fixedly held in the mounting fixture; and
at least one of the first, second, third and fourth side walls having an aperture extending therethrough, and a viewing window disposed in the aperture.

16. A test system for a battery module, comprising:
a housing having a bottom plate; and first, second, third and fourth side walls coupled to the bottom plate that define an interior region; the first and third walls being disposed substantially parallel to one another;
a mounting fixture configured to fixedly hold the battery module thereon, the mounting fixture coupled to the bottom plate within the interior region;
first, second, third and fourth coupling members, the first and second coupling members coupled to an upper end of the first wall, the third and fourth coupling members coupled to an upper end of the third wall;
a lid coupled to the housing utilizing the first, second, third and fourth coupling members;
a battery charging system configured to charge the battery module while the battery module is fixedly held in the mounting fixture; and
the plate portion of the lid having an aperture extending therethrough, and a viewing window disposed in the aperture.

* * * * *